US010052031B2

(12) United States Patent
Sharma et al.

(10) Patent No.: US 10,052,031 B2
(45) Date of Patent: Aug. 21, 2018

(54) DETERMINING FUNCTIONAL SEVERITY OF STENOSIS

(71) Applicant: Siemens Healthcare GmbH, Erlangen (DE)

(72) Inventors: Puneet Sharma, Monmouth Junction, NJ (US); Ali Kamen, Skillman, NJ (US); Max Schöbinger, Hirschaid (DE); Michael Scheuering, Nürnberg (DE); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 604 days.

(21) Appl. No.: 14/180,704

(22) Filed: Feb. 14, 2014

(65) Prior Publication Data
US 2014/0249399 A1    Sep. 4, 2014

Related U.S. Application Data (60) Provisional application No. 61/771,978, filed on Mar. 4, 2013.

(51) Int. Cl.
| | | |
|---|---|---|
| *A61B 5/02* | (2006.01) | |
| *A61B 5/00* | (2006.01) | |
| *A61B 6/03* | (2006.01) | |
| *A61B 6/00* | (2006.01) | |
| *G06T 7/00* | (2017.01) | |
| *A61B 8/06* | (2006.01) | |
| *A61B 8/00* | (2006.01) | |
| *G01R 33/563* | (2006.01) | |

(52) U.S. Cl.
CPC ........ *A61B 5/02007* (2013.01); *A61B 5/7246* (2013.01); *A61B 5/7278* (2013.01); *A61B 6/032* (2013.01); *A61B 6/037* (2013.01); *A61B 6/466* (2013.01); *A61B 6/503* (2013.01); *A61B 6/504* (2013.01); *A61B 6/507* (2013.01); *A61B 6/5217* (2013.01); *A61B 6/5235* (2013.01); *G06T 7/0012* (2013.01); *A61B 5/0035* (2013.01); *A61B 5/742* (2013.01); *A61B 8/06* (2013.01); *A61B 8/463* (2013.01); *A61B 8/466* (2013.01); *A61B 8/565* (2013.01); *G01R 33/56366* (2013.01); *G06T 2207/10104* (2013.01); *G06T 2207/10108* (2013.01); *G06T 2207/30048* (2013.01); *G06T 2207/30101* (2013.01)

(58) Field of Classification Search
None
See application file for complete search history.

(56) References Cited

U.S. PATENT DOCUMENTS

| 7,916,919 B2 | 3/2011 | Zheng et al. |
|---|---|---|
| 7,953,266 B2 | 5/2011 | Gulsun et al. |
| 8,010,175 B2 | 8/2011 | O'Donnell et al. |
| 8,073,227 B2 | 12/2011 | Gulsun et al. |
| 8,098,918 B2 | 1/2012 | Zheng et al. |
| 2011/0015520 A1 | 1/2011 | Meetz et al. |
| 2011/0103671 A1 | 5/2011 | Meetz et al. |
| 2012/0053918 A1 | 3/2012 | Taylor |
| 2013/0246034 A1 | 9/2013 | Sharma et al. |

FOREIGN PATENT DOCUMENTS

| CN | 102077249 | 5/2011 |
|---|---|---|
| WO | WO2013138428 A | 9/2013 |

OTHER PUBLICATIONS

Shi, "Review of zero-D and 1-D models of blood flow in the cardiovascular system," Biomedical engineering online, vol. 10(1), 38 pages, 2011.*
Steinman, "Image-based computational fluid dynamics modeling in realistic arterial geometries," Annals of biomedical engineering, vol. 30(4), p. 483-497, 2002.*
Pennati, "Mathematical modelling of the human foetal cardiovascular system based on Doppler ultrasound data," Medical engineering & physics, vol. 19(4), p. 327-335, 1997.*
S. Mantero, et al., "The coronary bed and its role in the cardiovascular system: a review and an introductory single-branch model," Journal of Biomedical Engineering, vol. 14, pp. 109-116, 1992.
C. Murray, "The physiological principle of minimum work: I. The vascular system and the cost of blood volume," In Proc. of the National Academy of Sciences of the United States, vol. 12, pp. 207-214, 1926.
Y. E Yoon, et al., "Non-invasive functional assessment using computed tomography: when will they be ready for clinical use?," Cardiovascular Diagnosis Therapy, vol. 2, No. 2, pp. 106-112, 2012.
L. Itu, et al., "A Patient-Specific Reduced-Order Model for Coronary Circulation," IEEE International Symposium on Biomedical Imaging, Barcelona, Spain, pp. 1-4, 2012.
S. Y. Chung, et al., "Comparison of Stress Perfusion MRI and SPECT for Detection of Myocardial Ischemia in Patients With Angiographically Proven Three-Vessel Coronary Artery Disease," AJR Am J Roentgenol:195, pp. 356-362, 2010.
N. H. J. Pijls, et al., "Functional Measurement of Coronary Stenosis," Journal of the American College of Cardiology, vol. 59, No. 12, pp. 1045-1057, 2012.

(Continued)

*Primary Examiner* — G Steven Vanni (57) ABSTRACT

A method for determining functional severity of a stenosis includes: (a) generating a simulated perfusion map from a calculated blood flow; (b) comparing the simulated perfusion map to a measured perfusion map to identify a degree of mismatch therebetween, the measured perfusion map representing perfusion in a patient; (c) modifying a parameter in a model used in calculating the blood flow when the degree of mismatch meets or exceeds a predefined threshold; (d) computing a hemodynamic quantity from the simulated perfusion map when the degree of mismatch is less than the predefined threshold, the hemodynamic quantity being indicative of the functional severity of the stenosis; and (e) displaying the hemodynamic quantity. Systems for determining functional severity of a stenosis are described.

20 Claims, 5 Drawing Sheets

(56) References Cited

OTHER PUBLICATIONS

Chinese Office Action dated Apr. 13, 2017 in corresponding Chinese Application No. 201410076070.5.
Chinese Office Action dated Aug. 2, 2016 in corresponding Chinese Application No. 201410076070.5.
Shi, et al; "Review of Zero-D and 1-D Models of Blood Flow in the Cardiovascular System"; 2011; from http://www.biomedIca!-engineering-online.com/content/10/1/33.

* cited by examiner

DETERMINING FUNCTIONAL SEVERITY OF STENOSIS

RELATED APPLICATION

This application claims the benefit of U.S. Provisional Application No. 61/771,978, filed Mar. 4, 2013. The entire contents of the provisional application are incorporated herein by reference, except that in the event of any inconsistent disclosure or definition from the present specification, the disclosure or definition herein shall be deemed to prevail.

TECHNICAL FIELD

The present teachings relate generally to the computation of hemodynamic quantities indicative of the functional severity of stenosis. These hemodynamic values may be used in the treatment and/or assessment of coronary artery disease (CAD).

BACKGROUND

Cardiac disease is the leading cause of death for men and women in the United States and accounts for at least 30% of deaths worldwide. Although recent medical advances have resulted in improvements in the diagnosis and treatment of complex cardiac diseases, the incidence of premature morbidity and mortality remains large, at least in part due to a dearth of accurate in vivo and in vitro estimates of patient-specific parameters indicative of a patient's anatomy, physiology, and hemodynamics.

Medical imaging-based techniques, such as myocardial perfusion imaging (MPI), may be used in clinical and pre-clinical settings to characterize the severity of stenosis (e.g., coronary stenosis, cerebral artery stenosis, etc.). Perfusion scanning may be implemented in a variety of ways, including as ultrasound perfusion, computed tomography (CT) perfusion, magnetic resonance (MR) perfusion, and nuclear medicine (NM) perfusion. The MPI procedure may be used to identify perfusion defects in rest and/or stress-induced images of the heart. Single photon emission computed tomography (SPECT) and positron emission tomography (PET) are two types of NM perfusion that have been used.

For single vessel disease, perfusion scanning may be sufficient to identify a culprit lesion responsible for causing an observed perfusion defect, and the culprit lesion may then be treated, for example, by percutaneous coronary intervention (PCI), coronary artery bypass graft (CABG) intervention, or another form of treatment. However, perfusion scanning techniques are not well suited to identifying culprit lesions in multi-vessel disease or in cases involving balanced ischemia (e.g., with left main disease in conjunction with other stenosis) since perfusion imaging provides relative perfusion values in overlapping perfusion territories that may be associated with more than one main vessel. As a result of the overlap, isolation of the hemodynamically significant lesion is difficult. Moreover, unless the culprit lesion is identified and differentiated from other lesions that may be present, the culprit lesion may not be properly treated.

SUMMARY

The scope of the present invention is defined solely by the appended claims, and is not affected to any degree by the statements within this summary.

The present teachings may be used to identify lesion-specific ischemia even in multi-vessel or balanced ischemia situation. A combination of perfusion scanning data, anatomical imaging of coronary vessels, and computational fluid dynamics (CFD) techniques is used. In some embodiments, methods in accordance with the present teachings may be used to determine the hemodynamic severity of individual epicardial lesions in the context of the perfusion defects observed in a perfusion scan.

By way of introduction, a computer-implemented method for determining functional severity of a stenosis in accordance with the present teachings includes: (a) generating, by a processor, a simulated perfusion map from a calculated blood flow; (b) comparing, by the processor, the simulated perfusion map to a measured perfusion map to identify a degree of mismatch therebetween, the measured perfusion map representing perfusion in a patient; (c) modifying, by the processor, a parameter in a model used in calculating the blood flow when the degree of mismatch meets or exceeds a predefined threshold; (d) computing, by the processor, a hemodynamic quantity from the simulated perfusion map when the degree of mismatch is less than the predefined threshold; and (e) displaying the hemodynamic quantity. The hemodynamic quantity is indicative of the functional severity of the stenosis.

A system for determining functional severity of a stenosis in accordance with the present teachings includes: (a) a processor; (b) a non-transitory memory coupled to the processor; (c) first logic stored in the memory and executable by the processor to cause the processor to generate a simulated perfusion map from a calculated blood flow; (d) second logic stored in the memory and executable by the processor to cause the processor to compare the simulated perfusion map to a measured perfusion map to identify a degree of mismatch therebetween, the measured perfusion map representing perfusion in a patient; (e) third logic stored in the memory and executable by the processor to cause the processor to modify a parameter in a model used in calculating the blood flow when the degree of mismatch meets or exceeds a predefined threshold; and (f) fourth logic stored in the memory and executable by the processor to cause the processor to compute a hemodynamic quantity from the simulated perfusion map when the degree of mismatch is less than the predefined threshold, the hemodynamic quantity being indicative of the functional severity of the stenosis.

A non-transitory computer readable storage medium in accordance with the present teachings has stored therein data representing instructions executable by a programmed processor for determining functional severity of a stenosis. The storage medium includes instructions for: (a) generating a simulated perfusion map from a calculated blood flow; (b) comparing the simulated perfusion map to a measured perfusion map to identify a degree of mismatch therebetween, the measured perfusion map representing perfusion in a patient; (c) modifying a parameter in a model used in calculating the blood flow when the degree of mismatch meets or exceeds a predefined threshold; (d) computing a hemodynamic quantity from the simulated perfusion map when the degree of mismatch is less than the predefined threshold; and (e) displaying the hemodynamic quantity. The hemodynamic quantity is indicative of the functional severity of the stenosis.

DETAILED DESCRIPTION

Anatomical data (e.g., for assessing epicardial stenosis) may be combined with functional data (e.g., for identifying perfusion defect) in hybrid imaging (e.g., SPECT-CT and PET-CT). Thus, a 17-segment myocardial bulls-eye plot or a variant thereof may be used to visualize the perfusion image, with each segment being associated with one or more coronary vessels. In such a way, a reversible defect observed on a stress perfusion image may be qualitatively associated with one or more epicardial vessels and its underlying stenosis in order to identify the culprit lesion. However, this type of association is oftentimes insufficient—particularly though not exclusively in the case of multi-vessel disease and/or balanced disease, wherein the perfusion defects occupy multiple overlapping segments of the myocardial bulls-eye plot.

By way of example, the perfusion scan of a patient with a 3-vessel disease having angiographically significant lesions in the RCA, LAD and LCx may show normal flow in the territories supplied by the LAD and perfusion defects in the inferolateral segments. This information is not lesion specific, however, and may not be used to assess the functional severity of the three lesions observable in the corresponding angiography images. Notwithstanding, the success of PCI and/or CABG intervention depends on identification of the ischemia-causing lesion—a task that may not be reliably achieved via mere qualitative interpretation of perfusion scans.

Methods and systems for identifying lesion-specific ischemia from myocardial perfusion imaging and anatomical imaging of coronary vessels have been discovered and are described herein. Methods in accordance with the present teachings are based on an underlying flow model that may be derived from computational fluid dynamics (CFD) techniques to assess the effect of a stenosis on the perfusion status of the myocardium. A perfusion image provides a status of the myocardium (e.g., both reversible and irreversible defects), and the information provided by the perfusion image may be used to iteratively tune the outlet boundary conditions of the flow model in the epicardial vessels. Thus, in accordance with the present teachings, a clinician may assess the hemodynamic severity of an individual stenosis in the context of the perfusion defects observed in a perfusion scan by iteratively tuning the boundary condition parameters of the flow computations until the results are in close agreement with the perfusion image (e.g., the ground truth).

It is to be understood that elements and features of the various representative embodiments described below may be combined in different ways to produce new embodiments that likewise fall within the scope of the present teachings.

Figure 1:
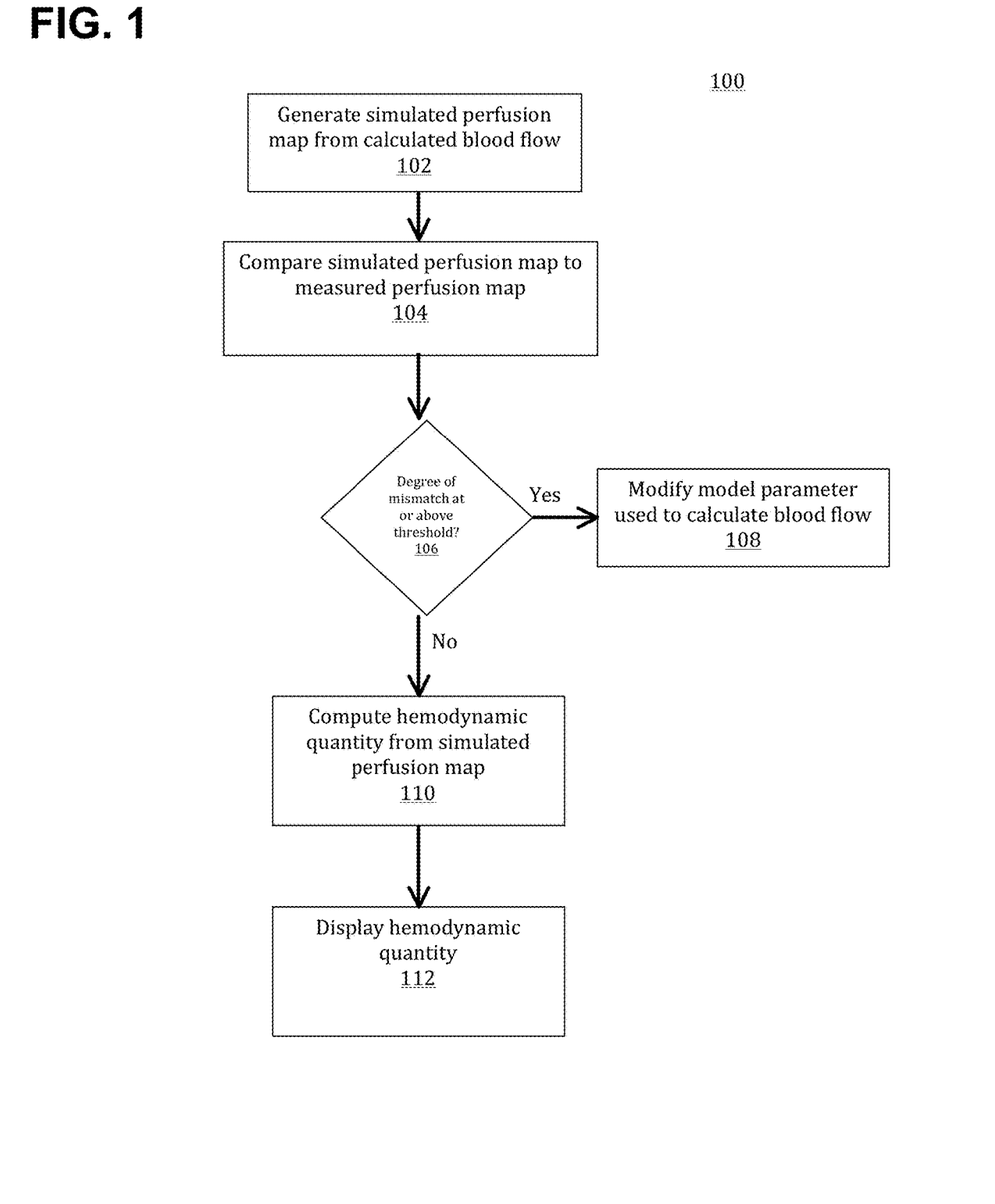
FIG. 1 shows a flow chart of an exemplary method for determining functional severity of a stenosis.

By way of introduction, as shown in FIG. 1, an exemplary method for determining functional severity of a stenosis in accordance with the present teachings includes: (a) generating 102 a simulated perfusion map from a calculated blood flow; (b) comparing 104 the simulated perfusion map to a measured perfusion map to identify a degree of mismatch therebetween, the measured perfusion map representing perfusion in a patient; (c) modifying 108 a parameter in a model used in calculating the blood flow when the degree of mismatch meets or exceeds a predefined threshold; (d) computing 110 a hemodynamic quantity from the simulated perfusion map when the degree of mismatch is less than the predefined threshold; and (e) displaying 112 the hemodynamic quantity. The determination as to whether the degree of mismatch meets or exceeds the predefined threshold may be made at decision block 106 as shown, for example, in FIG. 1.

In some embodiments, the hemodynamic quantity computed in accordance with the present teachings is indicative of the functional severity of the stenosis. As used herein, the phrase "hemodynamic quantity" refers broadly to any parameter relating to the flow of blood in the blood vessels. Representative "hemodynamic quantities" in accordance with the present teachings include but are not limited to blood flow velocity, blood pressure (or ratios thereof), heart rate, flow rate, fractional flow reserve (FFR), hyperemic stenosis resistance (HSR), index of myocardial resistance (IMR), and the like, and combinations thereof. In some embodiments, the hemodynamic quantity is computed from a blood flow value (e.g., flow rate and/or flow velocity) and/or a pressure value (e.g., a change in pressure) that may be derived from the simulated perfusion map.

All manner of stenosis is contemplated for assessment in accordance with the present teachings. Representative types of stenosis include but are not limited to coronary stenosis, cerebral artery stenosis, and the like, and combinations thereof.

In some embodiments, methods for determining functional severity of a stenosis in accordance with the present teachings may further include one or a plurality of additional acts, including but not limited to one or more of acts (f), (g), (h), and (i) described below. Different or fewer acts may be provided.

In some embodiments, methods in accordance with the present teachings further include (f) generating an anatomical model of a coronary vessel and/or of at least a portion of a myocardium based on medical imaging data acquired from a patient. Methods in accordance with the present teachings are independent of the type of medical imaging data that is used to generate the anatomical model of the coronary vessel and/or at least a portion of the myocardium. All manner of medical imaging modalities that are capable of providing anatomical information sufficient to initiate a domain are contemplated for use in accordance with the present teachings. Representative medical imaging data include but are not limited to magnetic resonance data, computed tomography data, single photon emission tomography data, ultrasound data, angiographic data, x-ray data, and the like, and combinations thereof. The medical imaging data may represent part of an interior region of a patient.

In some embodiments, the anatomical model includes a three-dimensional perfusion map, a two-dimensional polar perfusion map, or a combination of a three-dimensional perfusion map and a two-dimensional polar perfusion map. In some embodiments, methods in accordance with the present teachings further include (g) partitioning the anatomical model into a plurality of perfusion territories. The number of perfusion territories into which the anatomical model is partitioned is not restricted, and all manner of partitioning has been contemplated for use. In some embodiments, the anatomical model is partitioned into 16 segments (e.g., 16 left ventricular or LV segments) and, in some embodiments, the anatomical model is partitioned into 17 segments. In some embodiments, the segments into which the anatomical model are partitioned are selected from the group consisting of basal anterior, basal anteroseptal, basal inferoseptal, basal inferior, basal inferolateral, basal anterolateral, mid anterior, mid anteroseptal, mid inferoseptal, mid inferior, mid inferolateral, mid anterolateral, apical anterior, apical septal, apical inferior, apical lateral, apex, and combinations thereof.

In some embodiments, methods in accordance with the present teachings further include (h) applying a boundary condition at a boundary point of the coronary vessel. In some embodiments, the parameter to be modified at block 108 of FIG. 1 includes a boundary condition parameter. As used herein, the phrase "boundary point" refers to a point of a represented portion of a blood vessel, including but not limited to inflow points (inlets), outflow points (outlets), and junction points (e.g., bifurcations, trifurcations, quadfurcations, pentafurcations, hexafurcations, and the like, and combinations thereof). In some embodiments, the boundary point comprises an outlet. In some embodiments, the boundary condition is derived from perfusion data obtained from the measured perfusion map. In other embodiments, the boundary condition is obtained via allometric scaling.

In some embodiments, methods in accordance with the present teachings further include (i) performing a computational fluid dynamics (CFD) computation to obtain the blood flow and/or a pressure (e.g., one or both of which may be used to generate the simulated perfusion map).

The measured perfusion map to which the simulated perfusion map is compared may be obtained by all manner of perfusion scanning including but not limited to CT perfusion scanning, MR perfusion scanning, NM perfusion scanning, ultrasound perfusion, and the like, and combinations thereof. In some embodiments, the measured perfusion map is generated from myocardial perfusion imaging (MPI) data. In some embodiments, the MPI data may be derived from single photo emission computed tomography (SPECT), positron emission tomography (PET), or a combination thereof.

In some embodiments, a method for determining functional severity of a stenosis in accordance with the present teachings is implemented using a computer and, in some embodiments, one or a plurality of the acts of (a) generating 102, (b) comparing 104, (c) modifying 108, (d) computing 110, (e) displaying, (f) generating, (g) partitioning, (h) applying, and/or (i) performing described above may be performed by one or a plurality of processors and/or other devices controlled by a processor or processors.

In some embodiments, as described above, the present teachings provide methods for determining functional severity of a stenosis. In other embodiments, as further described below, the present teachings also provide systems for determining functional severity of a stenosis.

Figure 3:
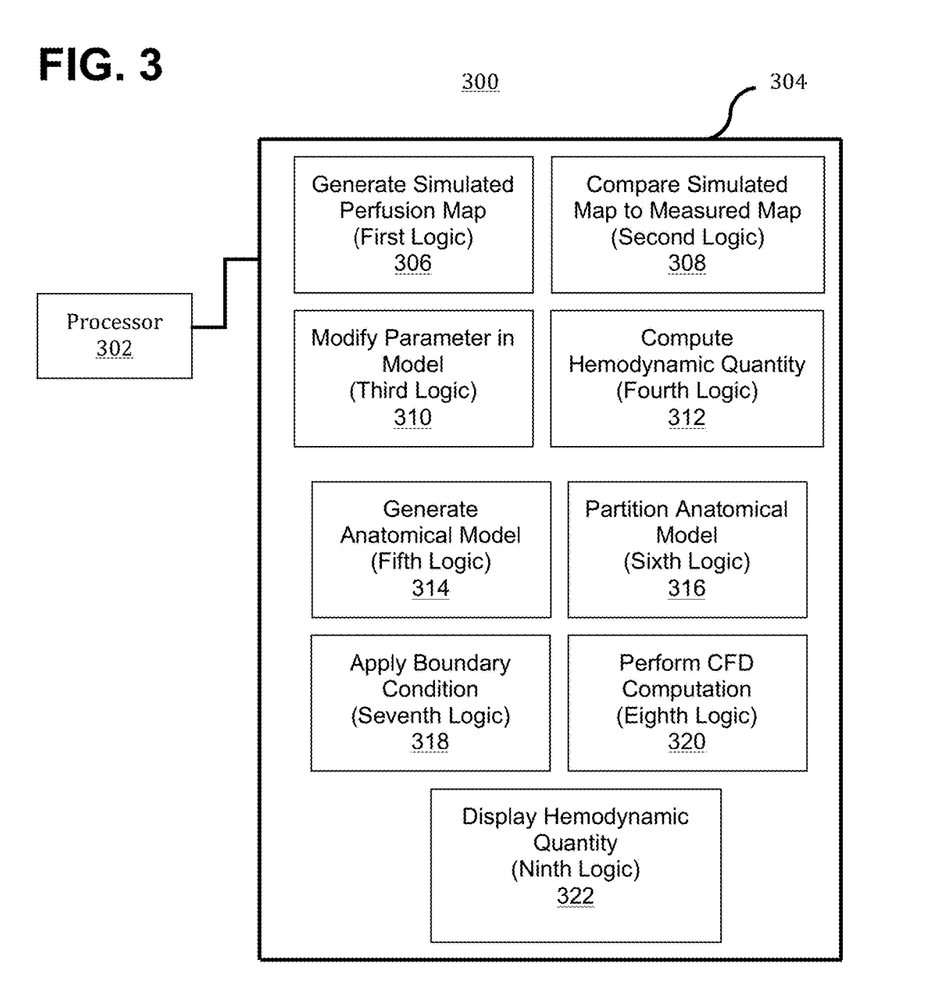
FIG. 3 shows a block diagram of an exemplary system 300 for determining functional severity of a stenosis.

FIG. 3 shows a block diagram of a representative system 300 for determining functional severity of a stenosis. In some embodiments, the system 300 may be implemented as part of a diagnostic and/or imaging module in a computer system, such as a personal computer, workstation, server, or computer in an imaging system.

As shown in FIG. 3, the exemplary system 300 includes: a processor 302; a non-transitory memory 304 coupled with the processor 302; first logic 306 stored in the non-transitory memory 304 and executable by the processor 302 to cause the processor 302 to generate a simulated perfusion map from a calculated blood flow; second logic 308 stored in the non-transitory memory 304 and executable by the processor 302 to cause the processor 302 to compare the simulated perfusion map to a measured perfusion map to identify a degree of mismatch therebetween, the measured perfusion map representing perfusion in a patient; third logic 310 stored in the non-transitory memory 304 and executable by the processor 302 to cause the processor 302 to modify a parameter in a model used in calculating the blood flow when the degree of mismatch meets or exceeds a predefined threshold; and fourth logic 312 stored in the non-transitory memory 304 and executable by the processor 302 to cause the processor 302 to compute a hemodynamic quantity from the simulated perfusion map when the degree of mismatch is less than the predefined threshold. In some embodiments, the hemodynamic quantity is indicative of the functional severity of the stenosis.

In some embodiments, as shown in FIG. 3, the system 300 may further include one or more of the following: fifth logic 314 stored in the non-transitory memory 304 and executable by the processor 302 to cause the processor 302 to generate an anatomical model of a coronary vessel and of at least a portion of a myocardium based on medical imaging data acquired from a patient; sixth logic 316 stored in the non-transitory memory 304 and executable by the processor 302 to cause the processor 302 to partition the anatomical model into a plurality of perfusion territories; seventh logic 318 stored in the non-transitory memory 304 and executable by the processor 302 to cause the processor 302 to apply a boundary condition at a boundary point of the coronary vessel; eighth logic 320 stored in the non-transitory memory 304 and executable by the processor 302 to cause the processor 302 to perform a CFD computation to obtain the blood flow and a pressure; and/or ninth logic 322 stored in the non-transitory memory 304 and executable by the processor 302 to cause the processor 302 to display the hemodynamic quantity. Fewer or different logic or instruction groupings may be provided.

In some embodiments, the system 300 may be coupled to other modules of a computer system and/or to databases so as to have access to relevant information as needed (e.g., medical imaging data, patient identification data, etc.) and initiate appropriate actions, such as connect with a picture archiving and communications system (PACS).

Figure 2:
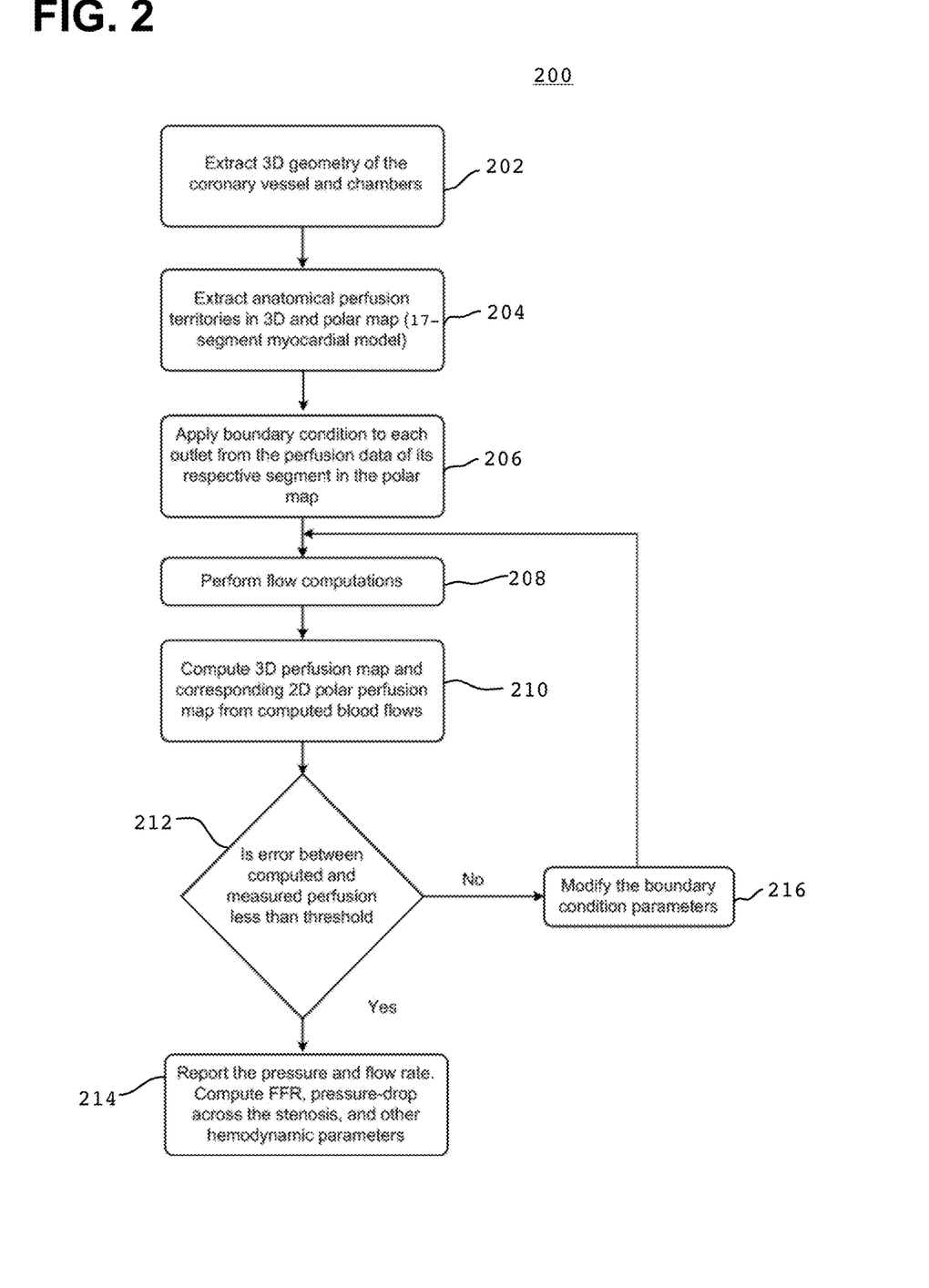
FIG. 2 shows a flow chart of another exemplary method for determining functional severity of a stenosis.

FIG. 2 depicts a flow chart showing an exemplary method 200 for determining functional severity of a stenosis that may be implemented, for example, using the representative system 300 shown in FIG. 3. As shown in FIG. 2, at block 202, the three-dimensional geometry of one or more coronary vessels and/or at least a portion of the myocardium may be extracted. By way of example, a three-dimensional anatomical model of the coronary vessels and the myocardium may be extracted from coronary CT angiography (CCTA) images as described, for example, in U.S. Pat. Nos. 7,916,919; 8,098,918; 8,073,227; and 7,953,266. In other embodiments, other types of medical imaging data, in addition to or alternatively to CCTA data, may likewise be employed. In some embodiments, the anatomical image of the coronary vessels and the perfusion image may be obtained from multi-modality sources, including but not limited to PET-CT, SPECT-CT, and/or other hybrid scans.

At block 204, the anatomical coronary territories may be identified. For example, a three-dimensional map of the coronary territories may be extracted from the cardiac image data, as described, for example, in U.S. Pat. No. 8,010,175.

To model the effect of the coronary microcirculation on the epicardial flow model, boundary conditions may be prescribed at each outlet of the coronary vessel. Accordingly, at block 206, the boundary conditions at the outlet of each coronary vessel may be estimated. In some embodiments, the outlet boundary conditions may be modeled as lumped models (e.g., a combination of resistance and capacitance elements) that take into account the pulsatile nature of the flow and the role of the microcirculatory resistance. In other embodiments, absent the perfusion status of the myocardium, the boundary conditions may be estimated from allometric scaling laws that prescribe a relationship between the diameter of the vessel at each outlet to the amount of flow carried thereby. In the case of patients with recent prior myocardial infarction, the vessels feeding the infracted zone remodel over several weeks or months. As a result, using the vessel caliber (e.g., diameter) to determine the boundary conditions according to the allometric scaling laws may result in overestimation in the flow and, therefore, an inaccurate assessment of the stenosis.

Similarly, the perfusion status of the myocardium may enhance the boundary conditions for patients with microvessel disease. Upon superimposing the epicardial coronary vessels on the two-dimensional polar plot (or three-dimensional territories), each coronary outlet will be associated with a myocardial segment. The perfusion status of this myocardium segment obtained from perfusion images may be used to determine the relative ratio of the resistance value that is specified at each outlet as the boundary condition.

At block 208 of FIG. 2, computations may be performed to compute coronary circulation. For example, numerical solution of the Navier-Stokes equation using CFD techniques may be used to determine the flow and pressure in the coronary circulation in the presence of patient-specific boundary conditions. The boundary condition at the inlet of the vessel tree may be determined either by coupling a lumped heart model or by directly specifying the total cardiac output at the aortic root. In some embodiments, the resting flow in the coronaries may be computed as a function of the myocardial mass and specified at the coronary inlet.

Figure 4:
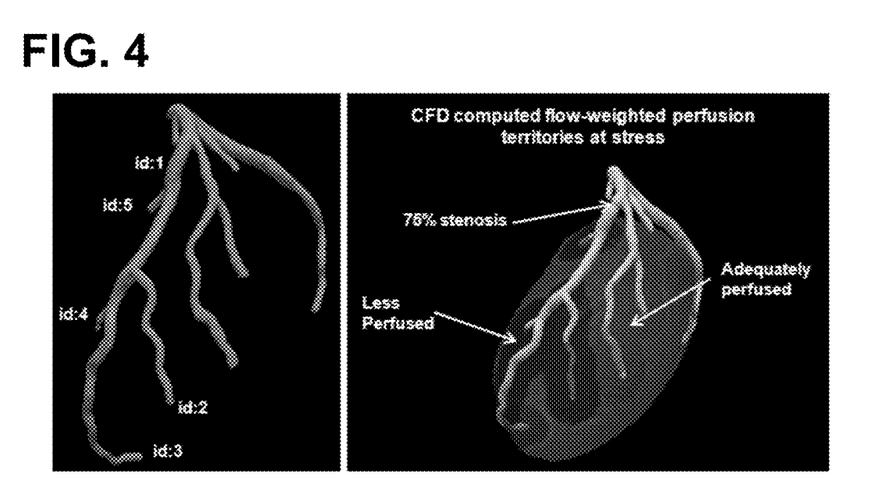
FIG. 4 shows an example of an anatomical model of epicardial coronary vessels (left), and an example of a simulated perfusion map obtained from a flow model (right).
Figure 5:
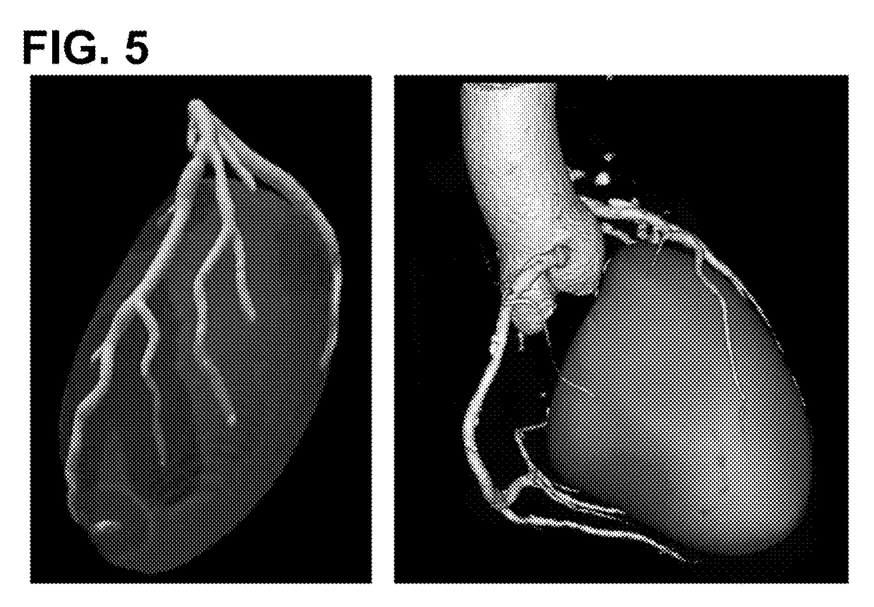
FIG. 5 shows an example of a simulated perfusion map obtained from flow computations (left), and an example of a measured perfusion map obtained from imaging (right).

At block 210, a simulated perfusion image may be computed from the calculated blood flow by analogy to act 102 of FIG. 1. For example, the blood flow rate computed at block 208 of FIG. 2 may be used to generate a simulated perfusion map of the myocardium. These simulated maps may be two-dimensional (e.g., in the form of a polar map) and/or three-dimensional, as shown in FIG. 4. The total flow (mL/min) at each outlet is divided by the mass of the myocardial (gm) subtended by that outlet to determine the perfusion value (mL/min/gm) of the corresponding myocardial segment. In some embodiments, for a more detailed computation of the perfusion, the myocardial tissue may be modeled as a porous medium or a poro-elastic medium, and the flow in the myocardial tissue computed accordingly. The inflow to the porous model is spatially distributed and may be determined from the flow computed at each outlet of the epicardial vessels.

At decision block 212 in FIG. 2, a determination is made as to whether the amount of error between the computed perfusion map and the measured perfusion map is less than a predefined threshold. In the case of three-dimensional perfusion maps, in some embodiments, the comparison may be made on a voxel-by-voxel basis. In the case of two-dimensional polar maps, in some embodiments, the comparison may be made on a segment-by-segment basis. In some embodiments, a segment-by-segment comparison of two-dimensional polar maps is less resource-intensive and/or time-consuming than an analogous voxel-by-voxel comparison of three-dimensional maps (e.g., 17 segments vs. millions of voxels). In some embodiments, different segments in two-dimensional polar maps may be weighted differently based on their importance, and weighted sums of the differences may be computed.

If the error at decision block 212 in FIG. 2 is greater than the predefined threshold, the process may proceed to block 216 and the boundary condition parameters may be modified. Based on the amount of mismatch between the observed and measured perfusion maps, the boundary conditions of each coronary outlet may be perturbed to iteratively minimize the mismatch. In some embodiments, the perturbation is based on the rationale that lowering the resistance value at an outlet will result in increased flow through that outlet, thereby resulting in an increased perfusion to the corresponding myocardial segment. In accordance with these principles, a parameter estimation procedure may be used to iteratively tune the boundary conditions until the resulting mismatch between the computed and measured perfusion maps is below the pre-defined threshold.

If the error between the computed and measured perfusion maps is less than the predefined threshold, the process may proceed to block 214 as shown in FIG. 2, and computations may be performed to assess hemodynamic lesion severity (e.g., FFR, stenosis pressure drop, and/or the like. For example, once the simulated perfusion image is in close agreement with the measured image, the resulting flow and pressure values in the epicardial vessels may be used to determine the hemodynamic severity of all of the stenoses. In some embodiments, fractional flow reserve (FFR) may be used to determine the hemodynamic severity of lesion. The FFR may be computed by taking the ratio of the average pressure distal to the stenosis with respect to the average pressure in the aorta. In some embodiments, other hemodynamic parameters—including but not limited to hyperemic stenosis resistance (HSR) and/or index of myocardial resistance (IMR)—may be computed from the flow and pressure value obtained from the CFD flow model either in addition to or as an alternative to computing the FFR.

In some embodiments, methods in accordance with the present teachings may be used for treating patients with histories of prior CABG, prior stenting, micro-vessel disease, prior MI, and/or the like. Methods in accordance with the present teachings may also be used for intervention planning, whereby a stenosis segment may be replaced by a healthy vessel, and the effect of the stenting procedure on the other vessels and stenosis investigated. In such embodiments, the radius of the healthy vessel may be computed by interpolating the proximal and distal radius of the stenosis segment under investigation.

It is to be understood that the relative ordering of some acts shown in the flow chart of FIGS. 1 and 2 is meant to be merely representative rather than limiting, and that alternative sequences may be followed. In some embodiments, acts may occur in a different sequential order and/or one or more of the acts may occur substantially contemporaneously. Moreover, it is likewise to be understood that additional, different, or fewer acts may be provided.

A non-transitory computer-readable storage medium in accordance with the present teachings has stored therein data representing instructions executable by a programmed processor for computing a hemodynamic quantity. The storage medium includes instructions for: (a) generating a simulated perfusion map from a calculated blood flow; (b) comparing the simulated perfusion map to a measured perfusion map to identify a degree of mismatch therebetween, the measured perfusion map representing perfusion in a patient; (c) modifying a parameter in a model used in calculating the blood flow when the degree of mismatch meets or exceeds a predefined threshold; and (d) computing a hemodynamic quantity from the simulated perfusion map when the degree of mismatch is less than the predefined threshold, the hemodynamic quantity being indicative of the functional severity of the stenosis.

One or more modules or logic described herein may be implemented using, among other things, a tangible computer-readable medium comprising computer-executable instructions (e.g., executable software code). Alternatively, modules may be implemented as software code, firmware code, hardware, and/or a combination of the aforementioned. For example the modules may be embodied as part of a medical imaging system.

Figure 6:
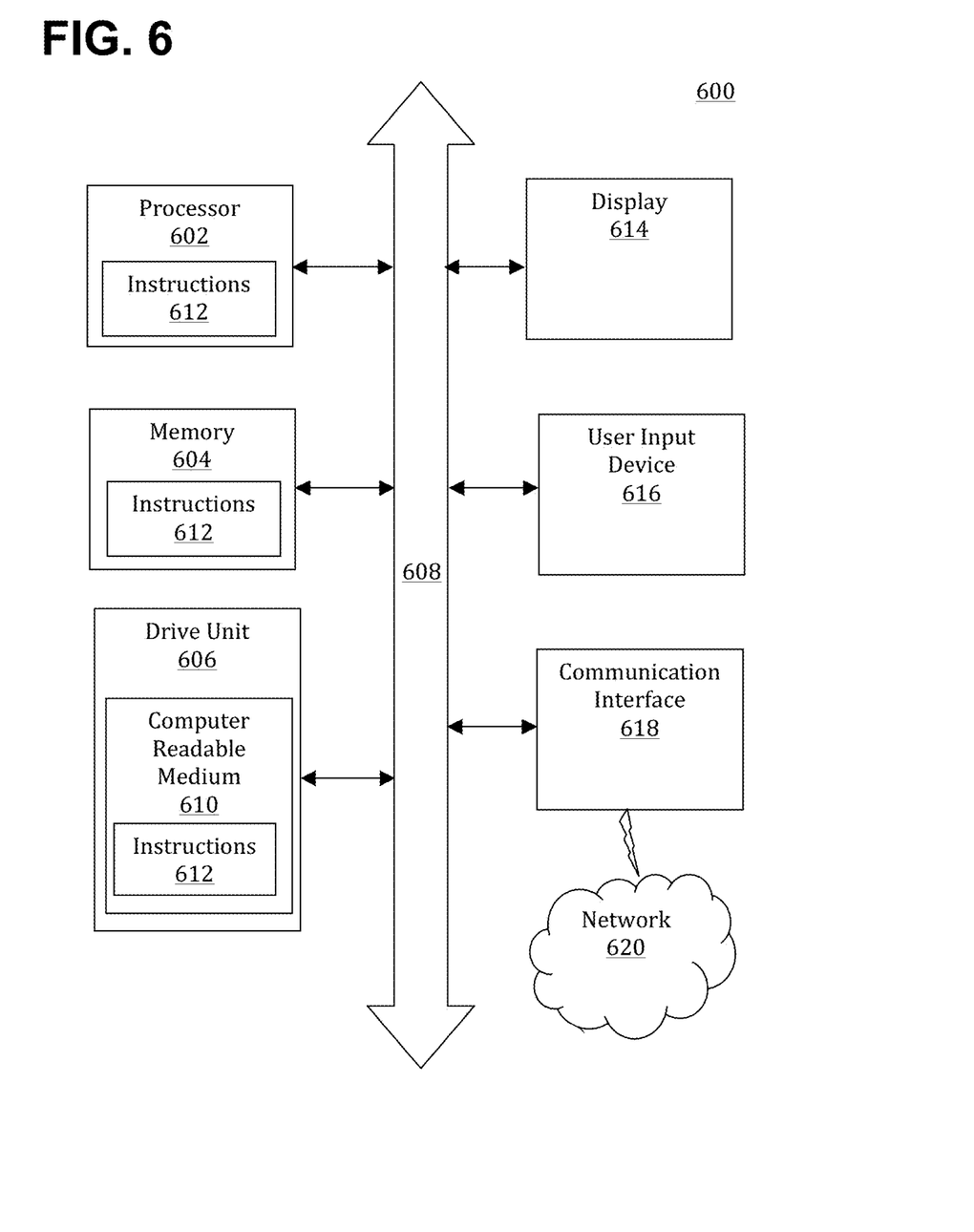
FIG. 6 shows an exemplary representative general computer system 600 for use with a system in accordance with the present teachings.

FIG. 6 depicts an illustrative embodiment of a general computer system 600. The computer system 600 can include a set of instructions that can be executed to cause the computer system 600 to perform any one or more of the methods or computer based functions disclosed herein. The computer system 600 may operate as a standalone device or may be connected (e.g., using a network) to other computer systems or peripheral devices. Any of the components discussed above, such as the processor, may be a computer system 600 or a component in the computer system 600. The computer system 600 may implement a modeling engine on behalf of a health care facility, of which the disclosed embodiments are a component thereof.

In a networked deployment, the computer system 600 may operate in the capacity of a server or as a client user computer in a client-server user network environment, or as a peer computer system in a peer-to-peer (or distributed) network environment. The computer system 600 may also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In some embodiments, the computer system 600 may be implemented using electronic devices that provide voice, video or data communication. Further, while a single computer system 600 is illustrated, the term "system" shall also be taken to include any collection of systems or sub-systems that individually or jointly execute a set, or multiple sets, of instructions to perform one or more computer functions.

As shown in FIG. 6, the computer system 600 may include a processor 602, for example a central processing unit (CPU), a graphics-processing unit (GPU), or both. The processor 602 may be a component in a variety of systems. For example, the processor 602 may be part of a standard personal computer or a workstation. The processor 602 may be one or more general processors, digital signal processors, application specific integrated circuits, field programmable gate arrays, servers, networks, digital circuits, analog circuits, combinations thereof, or other now known or later developed devices for analyzing and processing data. The processor 602 may implement a software program, such as code generated manually (i.e., programmed).

The computer system 600 may include a memory 604 that may communicate via a bus 608. The memory 604 may be a main memory, a static memory, or a dynamic memory. The memory 604 may include, but is not limited to, computer-readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In some embodiments, the memory 604 includes a cache or random access memory for the processor 602. In alternative embodiments, the memory 604 is separate from the processor 602, such as a cache memory of a processor, the system memory, or other memory. The memory 604 may be an external storage device or database for storing data. Examples include a hard drive, compact disc (CD), digital video disc (DVD), memory card, memory stick, floppy disc, universal serial bus (USB) memory device, or any other device operative to store data. The memory 604 is operable to store instructions executable by the processor 602. The functions, acts or tasks illustrated in the figures or described herein may be performed by the programmed processor 602 executing the instructions 612 stored in the memory 604. The functions, acts or tasks are independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

As shown in FIG. 6, the computer system 600 may further include a display unit 614, such as a liquid crystal display (LCD), an organic light emitting diode (OLED), a flat panel display, a solid state display, a cathode ray tube (CRT), a projector, a printer or other now known or later developed display device for outputting determined information. The display 614 may act as an interface for the user to see the functioning of the processor 602, or specifically as an interface with the software stored in the memory 604 or in the drive unit 606. A value or image based on the modeling may be output to the user on the display unit 614. For example, one or more hemodynamic quantities computed from the simulated perfusion map may be displayed on the display unit 614. Additionally or alternatively, an image representing part of the patient with modulation or alpha-numeric text representing a calculated value may be indicated in the image.

Additionally, as shown in FIG. 6, the computer system 600 may include an input device 616 configured to allow a user to interact with any of the components of system 600. The input device 616 may be a number pad, a keyboard, or a cursor control device, such as a mouse, or a joystick, touch screen display, remote control or any other device operative to interact with the system 600.

In some embodiments, as shown in FIG. 6, the computer system 600 may also include a disk or optical drive unit 606. The disk drive unit 606 may include a computer-readable medium 610 in which one or more sets of instructions 612 (e.g., software) may be embedded. Further, the instructions 612 may embody one or more of the methods or logic as described herein. In some embodiments, the instructions 612 may reside completely, or at least partially, within the memory 604 and/or within the processor 602 during execution by the computer system 600. The memory 604 and the processor 602 also may include computer-readable media as described above.

The present teachings contemplate a computer-readable medium that includes instructions 612 or receives and executes instructions 612 responsive to a propagated signal, so that a device connected to a network 620 may communicate voice, video, audio, images or any other data over the network 620. Further, the instructions 612 may be transmitted or received over the network 620 via a communication interface 618. The communication interface 618 may be a part of the processor 602 or may be a separate component. The communication interface 618 may be created in software or may be a physical connection in hardware. The communication interface 618 is configured to connect with a network 620, external media, the display 614, or any other components in system 600, or combinations thereof. The connection with the network 620 may be a physical connection, such as a wired Ethernet connection or may be established wirelessly as discussed below. Likewise, the additional connections with other components of the system 600 may be physical connections or may be established wirelessly.

The network 620 may include wired networks, wireless networks, or combinations thereof. The wireless network may be a cellular telephone network, an 802.11, 802.16, 802.20, or WiMax network. Further, the network 620 may be a public network, such as the Internet, a private network, such as an intranet, or combinations thereof, and may utilize a variety of networking protocols now available or later developed including, but not limited to TCP/IP based networking protocols.

Embodiments of the subject matter and the functional operations described in this specification may be implemented in digital electronic circuitry, or in computer software, firmware, or hardware, including the structures disclosed in this specification and their structural equivalents, or in combinations of one or more of them. Embodiments of subject matter described in this specification may be implemented as one or more computer program products, for example, one or more modules of computer program instructions encoded on a computer-readable medium for execution by, or to control the operation of, data processing apparatus. While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein. The computer-readable medium may be a machine-readable storage device, a machine-readable storage substrate, a memory device, or a combination of one or more of them. The term "data processing apparatus" encompasses all apparatuses, devices, and machines for processing data, including but not limited to, by way of example, a programmable processor, a computer, or multiple processors or computers. The apparatus may include, in addition to hardware, code that creates an execution environment for the computer program in question (e.g., code that constitutes processor firmware, a protocol stack, a database management system, an operating system, or a combination thereof).

In some embodiments, the computer-readable medium may include a solid-state memory such as a memory card or other package that houses one or more non-volatile read-only memories. Further, the computer-readable medium may be a random access memory or other volatile re-writable memory. Additionally, the computer-readable medium may include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the present teachings are considered to include any one or more of a computer-readable medium or a distribution medium and other equivalents and successor media, in which data or instructions may be stored.

In some embodiments, dedicated hardware implementations, such as application specific integrated circuits, programmable logic arrays and other hardware devices, may be constructed to implement one or more of the methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system encompasses software, firmware, and hardware implementations.

In some embodiments, the methods described herein may be implemented by software programs executable by a computer system. Further, in some embodiments, implementations may include distributed processing, component/object distributed processing, and parallel processing. Alternatively, virtual computer system processing may be constructed to implement one or more of the methods or functionality as described herein.

Although the present teachings describe components and functions that may be implemented in particular embodiments with reference to particular standards and protocols, the present invention is not limited to such standards and protocols. For example, standards for Internet and other packet switched network transmission (e.g., TCP/IP, UDP/IP, HTML, HTTP, HTTPS) represent examples of the state of the art. Such standards are periodically superseded by faster or more efficient equivalents having essentially the same functions. Accordingly, replacement standards and protocols having the same or similar functions as those disclosed herein are considered equivalents thereof.

A computer program (also known as a program, software, software application, script, or code) may be written in any form of programming language, including compiled or interpreted languages, and it may be deployed in any form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described herein may be performed by one or more programmable processors executing one or more computer programs to perform functions by operating on input data and generating output. The processes and logic flows may also be performed by, and apparatus may also be implemented as, special purpose logic circuitry, for example, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The main elements of a computer are a processor for performing instructions and one or more memory devices for storing instructions and data. Generally, a computer will also include, or be operatively coupled to receive data from or transfer data to, or both, one or more mass storage devices for storing data, for example, magnetic, magneto optical disks, or optical disks. However, a computer need not have such devices. Moreover, a computer may be embedded in another device, for example, a mobile telephone, a personal digital assistant (PDA), a mobile audio player, a Global Positioning System (GPS) receiver, to name just a few. Computer-readable media suitable for storing computer program instructions and data include all forms of non volatile memory, media and memory devices, including but not limited to, by way of example, semiconductor memory devices (e.g., EPROM, EEPROM, and flash memory devices); magnetic disks (e.g., internal hard disks or removable disks); magneto optical disks; and CD ROM and DVD-ROM disks. The processor and the memory may be supplemented by, or incorporated in, special purpose logic circuitry.

To provide for interaction with a user, some embodiments of subject matter described herein may be implemented on a device having a display, for example a CRT (cathode ray tube) or LCD (liquid crystal display) monitor, for displaying information to the user and a keyboard and a pointing device, for example a mouse or a trackball, by which the user may provide input to the computer. Other kinds of devices may be used to provide for interaction with a user as well. By way of example, feedback provided to the user may be any form of sensory feedback (e.g., visual feedback, auditory feedback, or tactile feedback); and input from the user may be received in any form, including but not limited to acoustic, speech, or tactile input.

Embodiments of subject matter described herein may be implemented in a computing system that includes a back-end component, for example, as a data server, or that includes a middleware component, for example, an application server, or that includes a front end component, for example, a client computer having a graphical user interface or a Web browser through which a user may interact with an implementation of the subject matter described in this specification, or any combination of one or more such back end, middleware, or front end components. The components of the system may be interconnected by any form or medium of digital data communication, for example, a communication network. Examples of communication networks include but are not limited to a local area network (LAN) and a wide area network (WAN), for example, the Internet.

The computing system may include clients and servers. A client and server are generally remote from each other and typically interact through a communication network. The relationship of client and server arises by virtue of computer programs running on the respective computers and having a client-server relationship to each other.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 CFR § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The entire contents of each and every patent and non-patent publication cited herein are hereby incorporated by reference, except that in the event of any inconsistent disclosure or definition from the present specification, the disclosure or definition herein shall be deemed to prevail.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

The invention claimed is:

1. A computer-implemented method for determining functional severity of a stenosis, the method comprising:
    generating, by a processor, a simulated perfusion map where perfusion in the simulated perfusion map is a function of a calculated blood flow and an anatomical model derived from medical imaging data from a patient;
    comparing, by the processor, the simulated perfusion map to a measured perfusion map, the measured perfusion map representing perfusion in the patient and obtained by perfusion scanning of the patient;
    identifying a degree of mismatch between, the simulated perfusion map and the measured perfusion map based on the comparing;
    determining whether the degree of mismatch between the simulated perfusion map and the measured perfusion map exceeds a predefined threshold;
    modifying, by the processor, a parameter in the anatomical model or a boundary condition of the anatomical model, the anatomical model used in calculating the blood flow when the degree of mismatch exceeds the predefined threshold;
    computing, by the processor, a hemodynamic quantity from the simulated perfusion map when the degree of mismatch is less than the predefined threshold, the hemodynamic quantity being indicative of the functional severity of the stenosis; and
    displaying the hemodynamic quantity indicative of the functional severity of the stenosis,
    wherein the hemodynamic quantity is a measure of a blood flow velocity, a vessel blood pressure, a blood pressure ratio, a blood flow rate, a fractional flow reserve, a hyperemic stenosis resistance, an index of myocardial resistance, or a combination thereof.

2. The computer-implemented method of claim 1 further comprising:
    generating, by the processor, an anatomical model of a coronary vessel and of at least a portion of a myocardium based on medical imaging data acquired from the patient.

3. The computer-implemented method of claim 2 wherein the medical imaging data comprises magnetic resonance data, computed tomography data, positron emission tomography data, single photon emission tomography data, ultrasound data, angiographic data, x-ray data, or a combination thereof.

4. The computer-implemented method of claim 2 wherein the anatomical model comprises a three-dimensional perfusion map, a two-dimensional polar perfusion map, or a combination thereof.

5. The computer-implemented method of claim 2 further comprising:
    partitioning, by the processor, the anatomical model into a plurality of perfusion territories.

6. The computer-implemented method of claim 5 wherein the anatomical model is partitioned into 17 segments.

7. The computer-implemented method of claim 1 further comprising:
    applying, by the processor, a boundary condition at a boundary point of the coronary vessel.

8. The computer-implemented method of claim 7 wherein the boundary point comprises an outlet.

9. The computer-implemented method of claim 7 wherein the boundary condition is derived from perfusion data obtained from the measured perfusion map.

10. The computer-implemented method of claim 7 wherein the boundary condition is obtained via allometric scaling.

11. The computer-implemented method of claim 1 further comprising:
    performing, by the processor, a Computational Fluid Dynamics (CFD) computation to obtain the blood flow and a pressure.

12. The computer-implemented method of claim 1 wherein the measured perfusion map is obtained via CT perfusion scanning, MR perfusion scanning, NM perfusion scanning, or a combination thereof.

13. The computer-implemented method of claim 1 wherein the measured perfusion map is derived at least in part from single photo emission computed tomography (SPECT) data, positron emission tomography (PET) data, or a combination thereof.

14. The computer-implemented method of claim 1 wherein the stenosis comprises a coronary stenosis, a cerebral artery stenosis, or a combination thereof.

15. The computer-implemented method of claim 1 wherein the parameter in the model comprises a boundary condition parameter.

16. The computer-implemented method of claim 1 wherein the hemodynamic quantity is computed from a blood flow value and/or a pressure value, and wherein the blood flow value and the pressure value are derived from the simulated perfusion map.

17. The computer-implemented method of claim 1 wherein the hemodynamic quantity comprises fractional flow reserve (FFR), hyperemic stenosis resistance (HSR), index of myocardial resistance (IMR), or a combination thereof.

18. A system for determining functional severity of a stenosis, the system comprising:
    a medical imaging system for perfusion scanning of a patient;
    a processor;
    a non-transitory memory coupled to the processor;
    first logic stored in the memory and executable by the processor to cause the processor to generate a simulated perfusion map where perfusion in the simulated perfusion map is a function of a calculated blood flow and an anatomical model derived from medical imaging data from a patient;

second logic stored in the memory and executable by the processor to cause the processor to compare the simulated perfusion map to a measured perfusion map, the comparison providing a degree of mismatch therebetween, the measured perfusion map representing perfusion in the patient as measured by the medical imaging system;

third logic stored in the memory and executable by the processor to cause the processor to determine whether the degree of mismatch between the simulated perfusion map and the measured perfusion map exceeds a predefined threshold;

fourth logic stored in the memory and executable by the processor to cause the processor to modify a parameter in a model used in calculating the blood flow when the degree of mismatch exceeds the predefined threshold;

fifth logic stored in the memory and executable by the processor to cause the processor to compute a hemodynamic quantity from the simulated perfusion map when the degree of mismatch is less than the predefined threshold, the hemodynamic quantity being indicative of the functional severity of the stenosis; and sixth logic stored in the memory and executable by the processor to cause the processor to display the hemodynamic quantity indicative of the functional severity of the stenosis.

wherein the hemodynamic quantity is a measure of a blood flow velocity, a vessel blood pressure, a blood pressure ratio, a blood flow rate, a fractional flow reserve, a hyperemic stenosis resistance, an index of myocardial resistance, or a combination thereof.

19. The system of claim 18 further comprising:

seventh logic stored in the memory and executable by the processor to cause the processor to generate an anatomical model of a coronary vessel and of at least a portion of a myocardium based on medical imaging data acquired from a patient;

eighth logic stored in the memory and executable by the processor to cause the processor to partition the anatomical model into a plurality of perfusion territories;

ninth logic stored in the memory and executable by the processor to cause the processor to apply a boundary condition at a boundary point of the coronary vessel;

tenth logic stored in the memory and executable by the processor to cause the processor to perform a CFD computation to obtain the blood flow and a pressure.

20. In a non-transitory computer readable storage medium having stored therein data representing instructions executable by a programmed processor for determining functional severity of a stenosis, the storage medium comprising instructions for:

generating a simulated perfusion map where perfusion in the simulated perfusion map is a function of a calculated blood flow and an anatomical model derived from medical imaging data from a patient;

comparing the simulated perfusion map to a measured perfusion map, the comparing providing a degree of mismatch therebetween, the measured perfusion map representing perfusion in a patient from a scan of the patient;

determining whether the degree of mismatch between the simulated perfusion map and the measured perfusion map exceeds a predefined threshold;

modifying a parameter in a model used in calculating the blood flow when the degree of mismatch exceeds a predefined threshold;

computing a hemodynamic quantity from the simulated perfusion map when the degree of mismatch is less than the predefined threshold, the hemodynamic quantity being indicative of the functional severity of the stenosis; and displaying the hemodynamic quantity indicative of the functional severity of the stenosis.

wherein the hemodynamic quantity is a measure of a blood flow velocity, a vessel blood pressure, a blood pressure ratio, a blood flow rate, a fractional flow reserve, a hyperemic stenosis resistance, an index of myocardial resistance, or a combination thereof.

\* \* \* \* \*